United States Patent [19]
Schmitt

[11] Patent Number: 5,267,854
[45] Date of Patent: Dec. 7, 1993

[54] MINIATURE ORTHODONTIC APPLIANCE

[76] Inventor: Rodney D. Schmitt, 5725 Paradise Dr., #140, Corte Madera, Calif. 94927

[21] Appl. No.: 879,769

[22] Filed: May 6, 1992

[51] Int. Cl.⁵ .................................................. A61C 3/00
[52] U.S. Cl. .............................................. 433/8; 433/9
[58] Field of Search ........................................ 433/8, 9

[56] References Cited

U.S. PATENT DOCUMENTS

| | | | |
|---|---|---|---|
| 4,165,561 | 8/1979 | Miller et al. | 433/9 |
| 4,369,033 | 1/1983 | Webb et al. | 433/9 |
| 4,661,059 | 4/1987 | Kanno | 433/9 |
| 4,819,316 | 4/1989 | Rossini et al. | 433/8 X |
| 4,826,430 | 5/1989 | Chen et al. | 433/8 |
| 4,842,513 | 6/1989 | Haarmann | 433/8 X |
| 5,095,602 | 3/1992 | Reher et al. | 433/8 X |

*Primary Examiner*—John J. Wilson
*Assistant Examiner*—Nicholas D. Lucchesi
*Attorney, Agent, or Firm*—Harold D. Messner

[57] ABSTRACT

The invention discloses a metal injected molded (MIM) orthodontic bracket that includes a plurality of raised posts buccolingually extending from a tooth abutting surface. Each post includes a root section having a base integrally formed with the tooth abutting surface and a apex section buccolingually extending from the root section. The apex section terminates a sharp, continuous parameter edge that was originally, smaller in all directions than the root section. However, in accordance with the invention, further cold working of such edges occurs whereby each edge is easily worked—at ambient temperatures—into a mushroom-shaped button having a worked edge larger in all directions than its associated root section. As a result, when the bracket is attached to a wearer's tooth, the buccolingually extending surface area of the worked posts coupled with the tooth abutting surface between adjacent posts, form a modified scalloped surface that can be attached to the patient's tooth face with a substantial addition to strength of the bond securing the bracket. The side surfaces also define opposed planar gingival and lingual edges, while the end surfaces define opposed planar mesial and distal edges that are non-rhomboidal. The modified scalloped surfaces provided by the raised posts is further characterized by the formation of TEE-shaped crest sections midway between adjacent posts, such crest sections buccolingually repeating at intervals along row, columnar and lateral directions of the bracket.

16 Claims, 4 Drawing Sheets

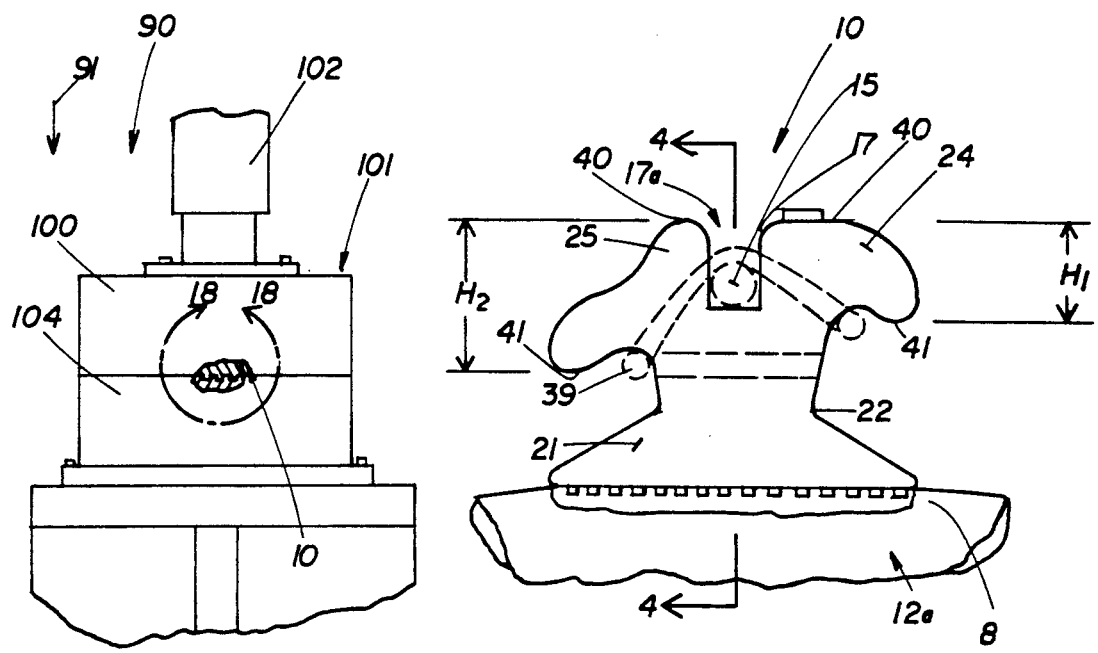
FIG. 17
FIG. 3
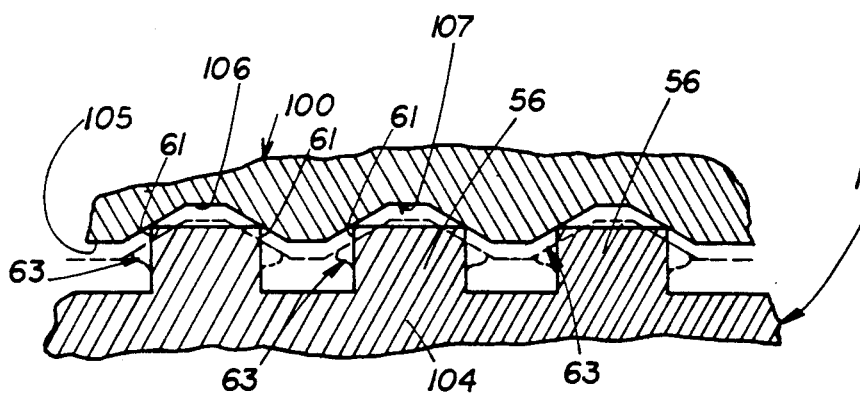
FIG. 18
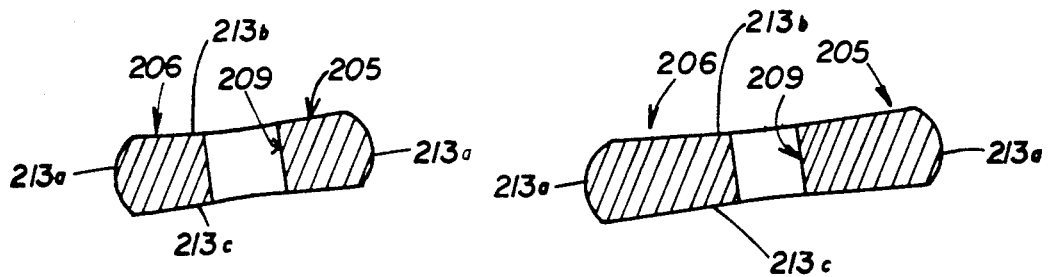
FIG. 14
FIG. 15

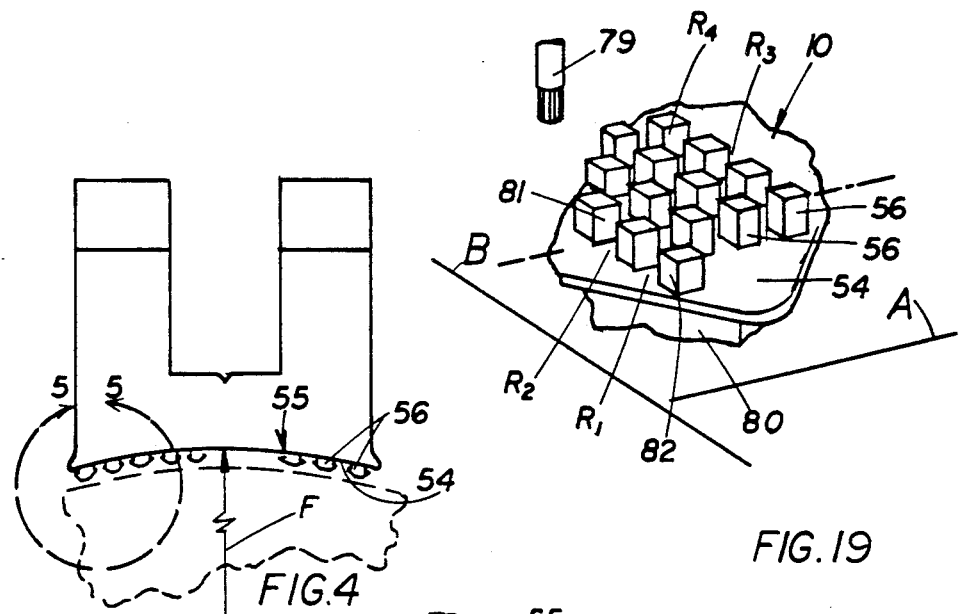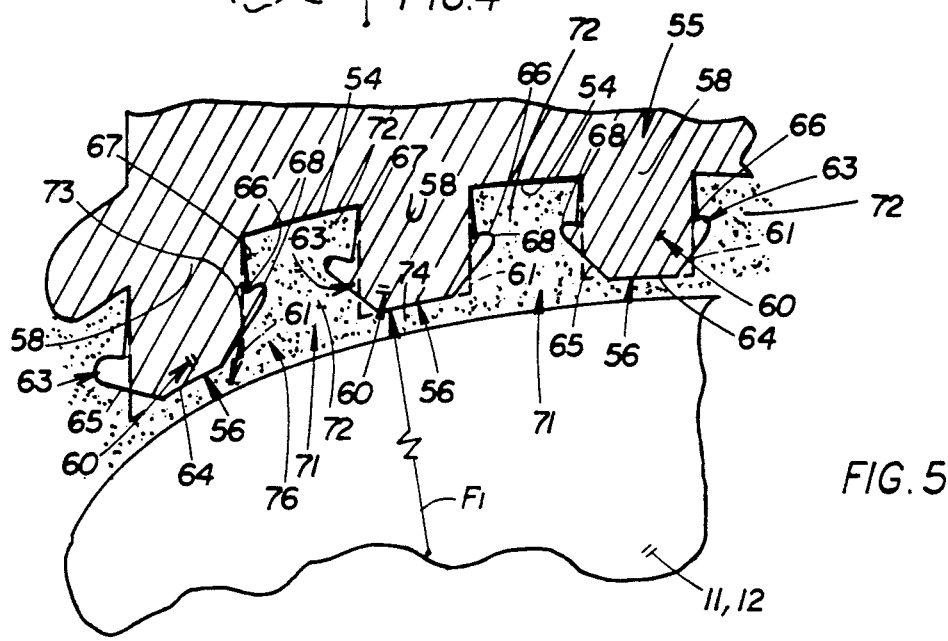

MINIATURE ORTHODONTIC APPLIANCE

SCOPE OF THE INVENTION

The present invention relates to orthodontic appliances and more particularly to miniature orthodontic brackets bonded by an adhesive to a patient's teeth.

In one aspect, the invention relates to a metal injected molded (MIM) orthodontic bracket that includes a plurality of raised posts. The plurality of posts extends from a tooth abutting surface and each includes a keystone or apex region terminating in a sharp parameter edge. Originally, such parameter edge was constructed to be smaller in all directions than its base or root section attached to the tooth abutting surface, say as the metal injection molding process terminates. However, in accordance with the present invention, further working of such edges of the posts can be easily provided whereby such parameter edges are reformed—at ambient temperatures—into a series of inverted, hood-like, mushroom-shaped buttons. Each button has a continuous edge larger in all directions than its base. As a result, the surface area of the worked posts and segmented portions of a curved tooth abutting surface form a modified scalloped surface that buccolingually extends relative to the tooth of the wearer to which the bracket is attached. The side surfaces define opposed planar gingival and occlusal edges, while the end surfaces define opposed planar mesial and distal edges.

In accordance with another aspect of the invention, the modified scalloped surfaces of the posts define enlarged TEE-shaped crest sections that buccolingually repeated at regular intervals along row, columnar and lateral directions across the bracket. Thus, there is a substantial increase in bonding strength since the length of the TEE-shaped crest sections are much longer than the height of each TEE arm. That is, rupture of the bond must be through a section of the bond itself during normal operations, say across the parallel arms of the TEE through finite sections of the bond. Since one of the arms will always be in compression when a turning moment is applied to the bracket, the strength of the bond is surprisingly good. The strength of the bonds remains even though erosion due to cleansing and usual masticatory activities, has occurred.

BACKGROUND OF THE INVENTION

Orthodontic brackets that are directly bonded to a patient's teeth, are now common. These brackets each typically include an archwire portion adapted to receive a straightwire and ligature ties to impart corrective force to the teeth and an integrally formed base pad portion. The base pad portion is formed opposite to the archwire portion and includes a tooth abutting surface shaped to conform to the shape of the wearer's teeth. This tooth abutting surface is adapted to be attached to the teeth using a non-toxic orthodontic adhesive.

Experience has shown that a common problem of such orthodontic brackets is the propensity of the base pad to break away from the tooth after bonding has occurred, and the skill required by the orthodontist to position the bracket relative to a wearer's tooth to impart corrective force without having portions of the bracket being brought into interfering contact with the wearer's gum, mouth etc. As to the former, cleaning of the wearer's teeth using a common tooth brush and cleaning paste, gel, powder and the like, for example, can erode the adhesive between the tooth and pad. In such weakened condition, the pad can be loosen from the tooth during normal masticatory activities. As to the latter situation, experience has also shown that when the gingival and occlusal tips of the L-shaped wing members are constructed in a rhomboidal configuration for alignment purposes, a series of sharp parameter edges are generated which can be a hazard to the wearer.

One approach to increase the bonding strength is described in U.S. Pat. No. 4,369,033 for "ORTHODONTIC BRACKET ASSEMBLY", Webb et al in which a series of cavities are formed in the tooth abutting surface of the pad during casting. While such cavities do increase the surface area of the pad and hence allow more adhesive (and surface area) adjacent to the surfaces to be bonded, the fact that the walls of the cavities must diverge outwardly at such surfaces, creates a mechanically weak joint, especially when twisting moments of force are applied to the bracket during masticatory activities including normal brushing. In such instances, such moment arms create large shear forces along longitudinal (as opposed to transverse) portions of the surfaces of the bracket to be bonded relative to the wearer's tooth.

GLOSSARY OF TERMS

In the present invention, the following terms shall have the following meanings:

a. "Gingival" shall denote that the gums of the wearer of the bracket of the invention are nearer to the modified combination than any other reference plane, stricture, axis or the like.

b. "Occlusal plane" is a generally horizontal plane through contacting surfaces of the bicuspid and molar teeth, occurring upon full closure of the wearer's jaws. Such plane includes the incisal edges of the anterior teeth such as the incisors and cuspids. As a modifier, "occlusal" also denotes that the occlusal plane is nearer the modified combination than any other reference structure, plane, axis or the like.

c. "Midplane" is a vertical plane that bisects the chin, mouth, nose and teeth of the wearer.

d. "Mesial" and "Distal" shall mean modifiers that denote direction relative to the midplane. As a modifier, "mesial" denotes that the modified combination is nearer to the midplane while "distal" means that the modified combination is further away relative to the midplane.

e. "Mesiodistally" means the modified combination extends in bidirections normal to the midplane.

f. "Buccolingual profile" denotes a profile of the bracket of the invention in which the bracket attached to a wearer's tooth is viewed normalized to the tongue of the wearer. As a modifier, "buccolingual" and "buccolingually" means the position of the modified combination relative to and normalized with respect to the wearer's tongue.

g. "Labiobuccal profile" denotes a profile of the bracket of the invention in which the bracket attached to a wearer's tooth is viewed normalized to the lips of the wearer. As a modifier, "labiobuccal" and "labiobuccally" means the position of the modified combination relative to and normalized with respect to the wearer's lip(s).

h. "Incisal edge of a tooth" means the edge where the crown connects to the face of the tooth.

j. "Crown of a tooth" means the top surface of a tooth.

j. "Long axis of a crown" denotes the axis of symmetry passing through the apex of the root through the crown of the tooth.

k. "Lingual" denotes that the position of the modified combination relative to and normalized with respect to the tongue of the wearer.

l. "Buccolabial" denotes the position of the modified combination relative to and normalized with respect to the lips of the wearer.

SUMMARY OF THE INVENTION

The present invention discloses a metal injected molded (MIM) orthodontic bracket that includes a plurality of raised posts buccolingually extending from a tooth abutting surface. Each raised post includes a root section having a base integrally formed with the tooth abutting surface and a keystone or apex section buccolingually extending from the root section. The keystone section terminates a sharp, continuous parameter edge. Originally, such parameter edge was smaller in all directions than the root section, say when the metal injection molding was completed. However, in accordance with the present invention, further cold working of such edges of the posts is provided whereby each parameter edge is easily worked—at ambient temperatures—into an inverted, hood-like, mushroom-shaped button having a worked continuous edge larger in all directions than its associated root section. As a result, when the bracket is attached to a wearer's tooth, the surface area of the worked posts and segmented portions of curved tooth abutting surface between adjacent posts, form a modified scalloped surface that extends buccolingually relative to the tooth face and substantially adds to the strength of the bond securing the bracket to such tooth. The side surfaces also define opposed planar gingival and lingual edges, while the end surfaces define opposed planar mesial and distal edges. In this regard, the modified scalloped buccolingual surfaces of the posts defines enlarged TEE-shaped crest sections that buccolingually repeat at regular intervals along row, columnar and lateral directions across the bracket. Since the length of the TEE-shaped crest sections are much longer than the height of each TEE arm, rupture of the bond must be through a section of the bond itself during normal operations, i.e., across the parallel arms of the TEE through finite sections of the bond. Since one of the arms will always be in compression when a turning moment is applied to the bracket, the strength of the bond is surprisingly good even after the bracket attached to the wearer's tooth has undergone usual erosion due to cleansing and usual masticatory activities.

In addition, the bracket of the invention also includes an labiobuccally extending, archwire portion that is opposite to the buccolingual scalloped surface, such archwire portion including a plurality of L-shaped wing members of at least four in number. The wing members are spaced along row and column directions to provide crossed-shaped intersecting grooves therebetween. One of the grooves forms a mesiodistally extending slot to capture a straightwire as well as defines a reference line (relative to the occlusal plane) by which the bracket can be correctly positioned in that dimension. While the other of the grooves provides a VEE those apex establishes a sight line for proper positioning of the bracket in a second dimension. The shape of such wing members is not rhomboidal, however. Any section through the gingival, mesiodistal and occlusally positioned edges of the wing members (as measured from a base reference plane) divides the mesiodistal edges into arcuate and planar pairs with respect to the slot which captures the straightwire. The apexes of such curved edges still provide positional guides since a line through such apexes are still parallel to the slot. Yet sharp parameter edges conventionally a part of rhomboidal shaped wing members are avoided. Some of the common profiles of L-shaped wing members of the present invention are standard profiles, low profiles, high profiles, high gingival wing profiles, and beveled occlusal wing profiles. As to the latter two type of profiles, assuming the tip of each wing member resembles a horse head in profile, the length of the horse heads in profile positioned on the same side relative to the straightwire relative to either the wearer's gums (gingival side) or the occlusal plane (occlusal side) can be shorter than that of members that are laterally positioned on a different side. In that way, the orthodontist has increased area along such side of the bracket viz., between the overhang of the more squat of the horse-head shaped members and the base pad, to attach the archwire assembly including the ligatory ties and straightwire relative to the bracket positional freedom is also provided wherein the bracket is not in contact with gums, mouth, lips etc. when the teeth are placed in the occlusal position.

As indicated above, it is preferred that the brackets be provided by a molding process wherein 60 percent by volume metal powder such as 316 stainless steel alloy having a particle size of less than 6 microns, is blended with a 40 percent by volume lubricating binder. The resulting mixture can be injected into a multi-cavitied mold in a manner similar to conventional plastic. The composition of the binder (viz., waxes and thermoplastics) provides the rheological capability of the mixture of flow around corners and into undercuts in a way that uniaxial pressing of lubricated metal powders of prior art methods, could never achieve. After the brackets have been removed from the mold, the wax is removed. Thereafter the bracket is sintered by conventional sintering processes using a belt, pusher or vacuum furnace. During heat-up, the remaining thermoplastics and lubricates are removed. Shrinkage of the brackets is variable, say less than 20 percent (normalized to a 60 percent bracket density). After sintering, the brackets attain near full density, say greater than 95 percent, and can be worked as by coining (a one-step stamping operation). In that way, the remote edges of each sintered post extending from the base of the bracket can be re-formed into an inverted, hood-like, mushroom-shaped button larger in all directions than the root section whereby the surface area of the worked posts and segmented portions of the curved tooth abutting surface between adjacent posts form a modified scalloped tooth abutting surface that increases the strength of bond when adhesive is used to secure the bracket to a patient's tooth. These posts are originally smaller in all directions than the bottom section after removal from the molding but are coinable into a series of umbrella-like hooded buttons in a single coining operation. In working the brackets at ambient temperature in the coining operation, they are first secured to a female member of a jig with the posts projecting away from its floor, and the male member of the jig is brought into working contact with the parameter edges (by hydraulic operation). Since the resulting compoundly curved, mushroom shaped buttons are each larger in all directions than the bottom section, the resulting modified scalloped tooth abutting surface (along columnar, row or lateral directions) increases bonding strength when an adhesive is used to secure the bracket to a wearer's tooth. One reason for the improvement relates to the fact that the shear forces acting at the tooth abutting surface of each bracket and the adhesive (created by moments of force occurring during subsequent use) are more easily resisted by the surface portion of the Tee-shaped crest defining the arms of the TEE since one surface arm is usually in compression while the other in tension under such circumstances.

The shape of the mold of the invention is the inverse of the that of the pre-worked brackets. Such mold includes, of course, a surface having the inverse shape of the tooth abutting surface and the uprising posts thereof. For forming such surface and posts, conventional steps for forming the mold are used wherein the length, width and depth of mold cavities (which form the posts of the invention) are carefully controlled.

To provide controls needed to form the cavities of the mold, the master bracket can be formed by machining operations in which the upright posts are formed using changing cutting planes of a cutting machine to cut the latter. After an initial cut is made, the jig (and posts) are usually indexed about an axis to provide for a different cutting plane in sequence. Thereafter, the master bracket has been machined and is used as a master guide to form the mold in conventional manner resulting in the provision of an inverse mold ready for production. Note that in the final of correct dimensions of the cavities of the mold, the side walls are larger at the bottom than at the top. Such shaping speeds release of the brackets from the mold prior to sintering since the posts of each of the molded brackets are larger at the bottom than at the top section.

The brackets of the invention are preferably molded in a muli-cavity mold as integral units. Provision of such brackets, viz., as integral units, allows each to be a miniature, strong and accurately reproduced unit at reasonable cost.

In the sintering process, various conventional processes can be used after the wax and/or thermoplastic binders and lubricants have been removed from the parts. In one process I know of, the wax is removed by a solvent and the remaining plastic binder is thermally removed during a controlled heat up of the furnace during sintering (a combination deplasticizing and sintering step) over a relatively long time period, say 3-5 days. In another process, the wax is removed in air at about 350 degrees F. over a 1 to 2 day period. Such removal step oxidizes the parts imparting extra strength. Sintering at conventional temperatures in a closed vessel in a controlled atmosphere of argon and hydrogen follows. In yet another process, methylcellulose along with small amounts of water, glycerine and boric acid, are used as the binder. After the parts are molded, the water is removed by dry heat at 250 degrees F. Sintering using belt, pusher or vacuum furnaces, follows in which the methylcellulose is easily removed during furnace heat up since the latter breaks down at such temperature and follows the channels in the part created by the evaporated water. In still another process, the binders and lubricants are removed in a single stage vacuum furnace. The parts are then sintered at temperatures of 1100 to 1300 degrees C.

The metal powder is stainless steel alloy having a particle size of less than 6 microns.

In working the posts after the molding process has been completed, a coining operation is used. Such operation is at ambient temperature and results in the re-formation of the parameter edges of the posts into hooded, mushroom-shaped buttons 65 of each bracket in a single unitary stamping operation. In coining, the male member of the jig attached to a arm of a stamping machine is moved a short distance say 0.003 inches into contact with sharp parameter edges of the posts of pre-positioned bracket. The surface of the male member is shaped in a series of scallops running in row, columnar and lateral directions of the finished buttons. Movement of the jig is controlled so the apex of the crest of the male member—at the end of the arm movement—is above the original height of the post but the arcuate up-and downwardly shape of the scallops are below such original height. The result is the deformation of the sharp parameter edges into a hooded, mushroom-shaped button in which the sintered metal comprising each sharp edge of each post is forced to conform to the shape of the crest section of the male jig member. The jig is manufactured to usual engineering standards. The female member is provided with a series of cavities to retain the brackets in correct alignment with the male member during rectilinear movement of the latter. A series of male studs in alignment with female openings in the members also aid to keep the male member aligned with the female member.

After the molded bracket has been worked in the coining operation, the worked bracket of the invention is next placed in a tumbler having an abrasive material to remove sharp edges and smooth the surfaces of the bracket. Smoothing of the sintered surfaces of the brackets is desirable for aesthetic reasons and for the comfort of the wearer. Thereafter the brackets can be placed in a second abrasive medium for polishing. During polishing, the surfaces of the bracket are further smoothed to the desired degree of luster. Both smoothing operations are inexpensive and very effective from an aesthetic point of view.

Other features and advantages of the present invention will appear from the following description in which the preferred embodiments have been set forth in conjunction with the following drawings.

BRIEF DESCRIPTION OF THE DRAWINGS

FIG. 3 is a side elevational view of the bracket of FIG. 2 showing the archwire assembly, adhesive and patient's tooth in phantom line;

FIG. 4 is a section taken along line 4—4 of FIG. 3;

FIG. 5 is an enlargement of FIG. 4 taken along line 5—5 of FIG. 4;

FIGS. 14 and 15 are sections taken along lines 14—14 and 15—15, respectively, of FIG. 13;

FIG. 16 is a detail bottom view of the bracket of FIG. 11;

FIG. 17 is a side elevational view of stamping machine, partially cut-away, attached to a male-female jig;

FIG. 18 is an enlarged view of the cut-away portion of FIG. 17, specifically taken along line 18—18 thereof;

FIG. 19 is an enlarged perspective view of the tooth abutting surface of each bracket prior to the coining operation in which the posts are rectangular or square in cross section; and FIG. 20 is second enlarged perspective view of an alternate tooth abutting surface prior to the coining operation in which the posts are circular in cross section.

PREFERRED EMBODIMENTS OF THE INVENTION

Figure 1:
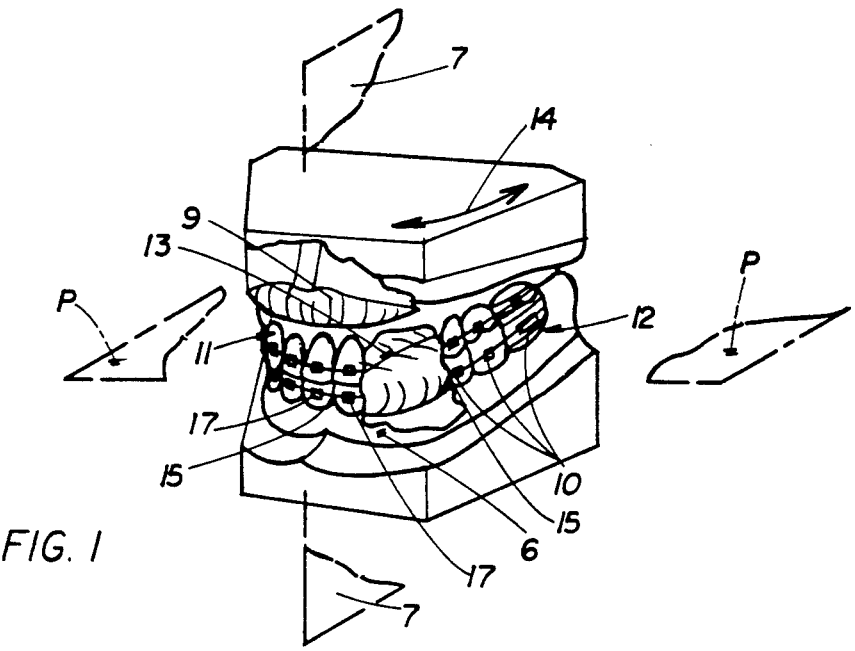
FIG. 1 is a perspective view of a series of orthodontic brackets of the invention attached to a patient's teeth, each of such brackets including a straightwire and elastic ties forming the archwire assembly by which the wearer's teeth are stressed relative to a series of reference axes to straighten them.

FIG. 1 shows a series of orthodontic brackets 10 of the invention attached to upper and lower teeth 11, 12 relative to a patient's lips 9 and tongue 13 broken away to better illustrate the invention. The upper teeth 11 are fixed to the upper jaw or maxilla (not shown) and are commonly termed maxillary teeth. The lower teeth 12 are affixed to the lower jaw or mandible (also not shown) and are commonly termed mandibular teeth. Each of the maxillary and mandibular teeth 11, 12 include a pair of central incisors, lateral incisors, cuspids, first bicuspids, second bicuspids, first molars, second molars and third molars. Hence there are normally thirty-two such teeth in all of which eight are on each side of each lower and upper dental arch 14. In FIG. 1 such teeth 11, 12 are shown in an occluded or closed position to define an occlusal plane P. The brackets 10 of the invention attach to the teeth 11, 12 at locations that are related to the occlusal plane P, gum tissue or gingiva 6, vertical midplane 7 bisecting dental arch 14 (a mesial direction is toward the midplane 7 and a distal direction is away from the plane 7), and the root axes of the teeth 11, 12. Note also that the midplane 7 and occlusal plane P as well as the position of the wearer's lips 9, tongue 13 and gums 6 also define the buccolingual and labial positions relative to particular description of the brackets 10 of the invention. I.e., the buccolingual profile of the bracket 10 is a side view toward or away from the midplane 7 normalized to the wearer's tongue 13. The labial profile is a view of the bracket 10 normalized to the wearer's lips 9. Edges of the brackets 10 are likewise descriptive based upon relative position with respect to the wearer's gums 6, lips 9, tongue 13, midplane 7 and occlusal plane P. I.e., labiobuccal edges would be nearer to the lips 9, while buccolingual edges would be near the tongue 13. Likewise, gingival edges would be nearer the gums 6, while occlusal edges would be nearer to the occlusal plane P. Mesiodistal positioned edges would be edges measured with respect to the midplane 7.

Semi-permanent bonding of the brackets 10 of the invention at such locations is carried out using a common non-toxic, manually removal orthodontic bonding adhesive such as conventionally available in the trade, such as TRANSBOND, UNITE or CONCISE all tradenames of the 3M Company, Minneapolis, Minn. The bonding strength of such group of adhesives is controlled such that shear strength is less than that of the enamel of the teeth 11, 12 to which the brackets 10 attached.

A mesodistally extending slot 17 is used to capture a straightwire 15 at the center of the brackets 10 whereby the axis of symmetry of the straightwire 15 establishes a line of reference that is aligned parallel to occlusal plane P of the teeth 11, 12. Such slot 17 is buccalabially positioned so that the orthodontist is unhindered in his application of forces via the brackets 10 to the teeth 11, 12 to bring about corrective realignment as explained below.

Figure 2:
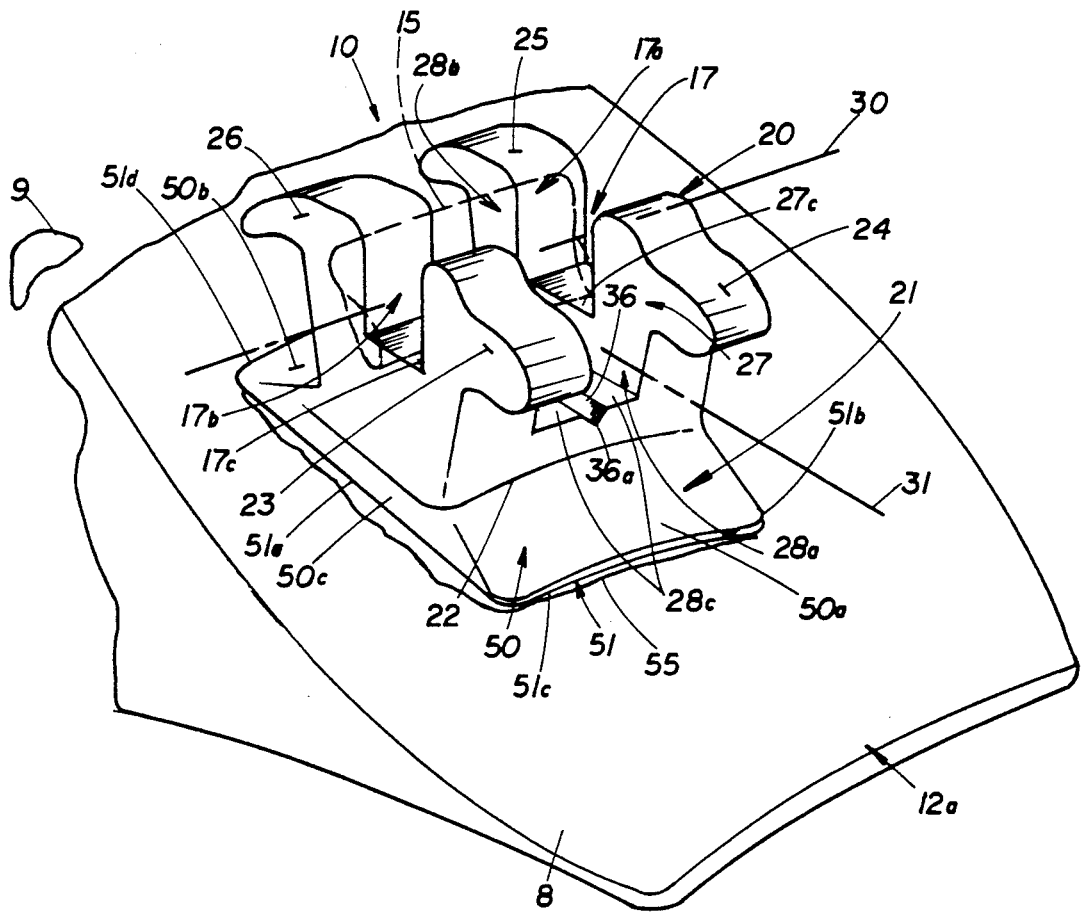
FIG. 2 is an enlarged perspective view of a single orthodontic bracket in which the illustrated bracket has been rotated approximately 90 degrees from that of FIG. 1 and has a portion of the archwire assembly shown in phantom line.

FIG. 2 illustrates one form of the orthodontic bracket 10 of the invention in more detail wherein such form is a standard profile bracket 10 shown attached to a tooth face 8 which has been rotated ninety degrees from the perspective view of FIG. 1. For purpose of discussion, assume the tooth face 8 is associated with a lower tooth 12a of the wearer of FIG. 1.

As shown, each bracket 10 includes a labiobuccally positioned archwire portion 20 adapted to receive the mesodistally extending straightwire 15. The archwire portion 20 is attached to a buccolingually positioned base pad 21 at neck segment 22 and includes a plurality of L-shaped wing members 23, 24, 25 and 26 separated one from the other, by the slot 17 previously mentioned as well as by a cross groove generally indicated at 27.

In general, the slot 17 establishes a reference line (relative to the occlusal plane P of FIG. 1) by which the bracket 10 can be correctly positioned in that dimension. The cross groove 27 provides a sight line for proper positioning of the bracket in a second dimension.

Now in more detail, the slot 17 includes arms 17a, 17b while the groove 27 defines arms 28a, 28b. The arms 17a, 17b and 28a, 28b define separate axes of symmetry 30, 31 that are perpendicular to each other. That is to say, the arm 17a is seen to extend between and be defined by the L-shaped members 24, 25 while the arm 17b is seen to extend between the L-shaped members 23, 26. The arms 17a, 17b are parallel to and coextensive with each other. Thus, their axes of symmetry 430 are commonly positioned in a collinear manner. Together the arms 17a, 17b form the slot 17 to receive the straightwire 15.

In similar fashion, the arm 28a of the groove 27 is seen to extend between and be defined by the L-shaped members 23, 24 while the arm 28b is seen to extend between the L-shaped members 25, 26. Thus the arms 28a, 28b are parallel to and coextensive with each other, but are normal to arms 17a, 17b. But base 28c of the arms 28a, 28b is not coextensive with base 17c of the arms 17a, 17b.

In FIG. 2, note that groove 27 includes a VEE 36 across base 28c that includes an apex 36a that defines a sight line along the apex 36a by which the orthodontist establishes reference planes relative to the crown axis of reference of the tooth 12a. Such crown axis of reference is well-known to the orthodontist skilled in the art and aids him in establishing correct location between the bracket 10, tooth 12a and the reference axis to bring about correct re-alignment of the tooth 12a.

FIG. 2 also shows that the base pad 21 includes a series of slanted faces 50 extending between neck 22 and terminal edges generally indicated 51. Two of the faces of opposite sides relative to the neck segment 22, viz., faces 50a, 50b have a more shallow angle that the angle of the remaining faces 50c. The terminal edges 51 also form the edges of a convexly shaped, buccolingually positioned tooth abutting surface 55, such convex shaped being established relative to the neck 22. Opposite edges 51a, 51b are not parallel to each other but lie in a common plane, while edges 51c, 51d are also not parallel to each other although they also lie in the same common plane.

Figure 6:
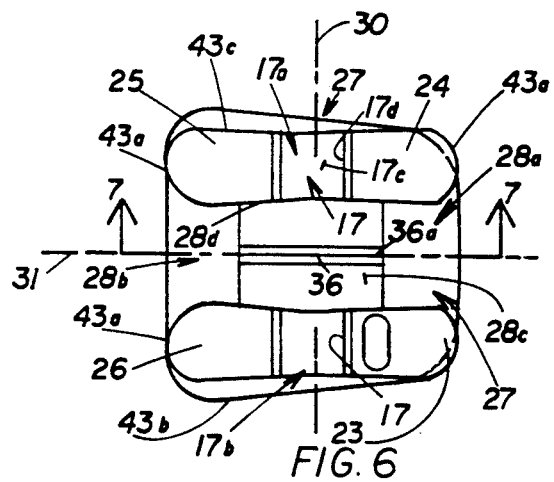
FIG. 6 is a detail top elevation view of the bracket of the invention of FIG. 3 in which the archwire assembly, adhesive and patient's tooth have been omitted.
Figure 7:
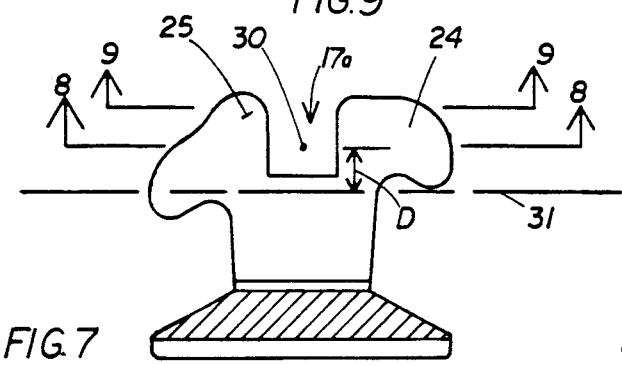
FIG. 7 is a section taken along line 7—7 of FIG. 6.

FIGS. 6 and 7 show the slot 17 and crossed groove 27 in further detail.

As shown note that even though the common axis of symmetry 31 of the arms 28a, 28b are parallel to and extensive with each other, such axes of symmetry 31 do not meet or intersect with the axes of symmetry 30 of the arms 17a, 17b, see especially FIG. 7. At their closest position such defined axes of symmetry 30, 31 are separated by a transverse distance D as shown.

As shown in FIG. 6, the arms 17a, 17b also includes side surfaces 17d of the arms 17a, 17b. Also the arms 28a, 28b comprise side surfaces 28d. Also note that the base 28c of the arms 28a, 28b is the VEE groove 36 and apex 36a previously mentioned.

FIG. 3 shown the positioning of the straightwire 15 in more detail.

As shown in FIG. 3, the arm 17a is seen to extend from between the L-shaped members 24, 25 to accommodate straightwire 15 shown in phantom line. Also seen in phatom line is tie 39 that extend over atop the straightwire 15 and thence about crowns 40 and overhangs 41 of the members 24, 25 to create sufficient force relative to tooth face 8 of tooth 12a. The heights H1 and H2 between the crowns 40 of the members 24, 25 with respect to the overhangs 41 are different, however. That is, H2>H1. In that way, the orthodontist has increased space relative to and along the gingival side of the bracket 10, viz., between the overhangs 41 of the more squat member 24 relative to base pad 21. That is, the gingival space between the overhangs 41 associated with crown height H1 of the member 24 relative to neck segment 22, is greater than the open space associated with the member 25. The increased open space allows the orthodontist to more easily attach the ties 39 and straightwire 15.

Figure 9:
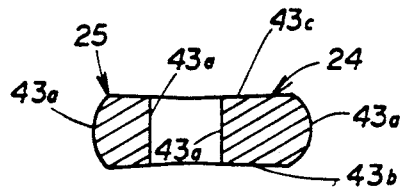
FIGS. 8 and 9 are sections taken along lines 8—8 and 9—9, respectively, of FIG. 7.
Figure 8:
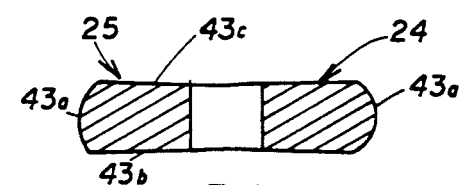

In addition, the pairs of members 23-26, viz., pair members 23, 26 and 24, 25 in plan view are not rhomboidal. Note in FIGS. 6, 8 and 9 that any section through the mesodistally, occlusally and gingivally positioned surfaces 43a, 43b and 43c of the wing members 24, 25 and 23, 26 divides the mesodistally positioned surfaces 43a into pairs of arcuate and planar edges. However, the apexes of the arcuate edges still provide positional guides since a line through the apexes are still parallel to the sight line previously mentioned. Yet sharp parameter edges conventionally a part of rhomboidal shaped wing members are avoided.

That is to say, the surfaces 43a of the pair members 24, 25 (or 23, 26) are arcuate with respect to the surfaces 43b, 43c. Also the non-rhomboidal shape remains irrespective of the cutting horizontal plane through the pair members 24, 25 (or 23, 26, as seen by comparing the sectional shapes of FIG. 8 with FIG. 9.

Figure 10:
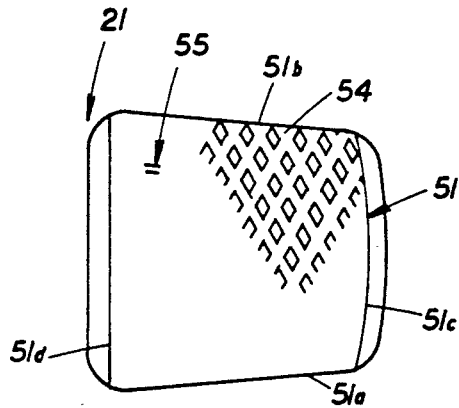
FIG. 10 is a bottom elevation view of the bracket of the invention of FIG. 5.

FIGS. 4, 5 and 10 shown the tooth abutting surface 55 of the pad 21 in more detail.

FIG. 10 shows that abutting surface 55 is not rhomboidal. That is, in FIG. 10, the opposite edges 51a, 51b are not parallel to each other but lie in a common plane, while edges 51c, 51d are also not parallel to each other although they also lie in the same common plane.

FIGS. 4 and 5 show the shape and character of the tooth abutting surface 55. Note that extending from curved base 54 of the tooth abutting surface 55 are a series of buccolingually extending, raised posts 56. The posts 56 also having a common radius of formation F1, see FIG. 5. Each raised post 56 includes a root section 58 integrally formed with respect to the curved elongated planar base 54 of the tooth abutting surface 55. A roof section 60 extends from the root section 58 and completes each of the posts 56. The roof sections 60 originally includes sharp parameter edges 61 shown in phantom line that were smaller in all directions than the root sections 58. Such edges 61 although originally smaller in all directions than the root section 58, are re-shaped as set forth below into inverted, anchor-like, mushroom-shaped buttons or cusps 63 larger in all directions than the root sections 58. The process of re-formation is set forth in detail below.

Each of the buttons or cusps 63 comprises a transversely flat, lingually extending apex region 64, a series of sloped segments 65 mesodistally extending away from the apex region 64 and terminating in eave segments 66. The eave segment 66 includes an overhang defining a circumferential edge 68 having a transverse dimension that is greater than that of the root section 58.

Note also in FIG. 5 that the total bondable surface area formed between the cusps 63 of the worked posts 56 and the adjacent segmented curved base 54, form a modified scalloped tooth abutting surface generally indicated at 71. Such scalloped abutting surface 71 is in three dimensions radiating from any of the posts 56 in row, columnar and lateral directions for improved disconnectable attachment of the bracket 10 of the invention to a patient's tooth 11, 12. But in FIG. 5, only a single scalloped abutting surface 71 is shown in section along one of the row, column or lateral directions previously mentioned. Note that in such configuration each scalloped abutting surface 71 (normalized between any two adjacent posts 56) comprises an enlarged, mesiodistically extending TEE-shaped crest sections 72 formed between end sections 73, 74. The trio of elements is then repeated at the same intervals along the chosen direction of interest viz., along the chosen row, columnar and lateral direction of interest through the extending posts 56 marking that direction. In such row, columnar or lateral direction, note that TEE-shaped crest section 72 includes adjacent surfaces of neighboring side-by-side posts 56 and the tooth abutting surface 55 as follows: along the apex region 64, thence along the sloped roof segments 65 extending away from the apex regions 64, along and about eave segments 66, along side surfaces 67 of the root sections 58 and finally along the curved planar base 54 of the tooth abutting surface 55 between the posts 56 in the chosen direction of interest.

Since the length of the TEE-shaped crest sections 72 are longer than the height of each TEE arm along and about eave segments 66, rupture of adhesive generally indicated at 76 is by layered rupture in a region between the posts 56 and the wearer's tooth 11, 12. Such rupture must be through a section of the adhesive 76 itself. During normal operations, such rupture would be adjacent to the side surfaces 67 of the root sections 58 through layers of the adhesive 76. Since one of the arms of the TEE section 72 will always be in compression when a turning moment is applied to the bracket 10, the strength of the dried adhesive 76 in association with the scalloped surface 71 is surprisingly good even after the bracket 10 attached to the wearer's tooth 11, 12 has undergone usual erosion due to cleansing and usual mastatory activities.

METHOD OF MANUFACTURE

The shape of the mold of the invention is the inverse of the that of the pre-worked brackets 10. Such mold includes, of course, a series of complexly formed surfaces having the inverse shape of the bracket 10. For forming such surfaces, conventional steps for forming the mold are used wherein the length, width and depth of mold cavities (which form the posts 56 of the invention) are carefully controlled.

To provide controls needed to form the cavities of the mold, a master bracket in the form previously described can be formed by machining operations in which the upright posts 56 such as shown in FIGS. 19 and 20 are formed using changing cutting planes of a cutting machine to cut the latter. Referring now to FIG. 19, an initial cut is made by cutter 79. Thereafter, the entire jig 80 (and bracket 10 including posts 56) are usually indexed about an axis A relative to the cutter 79 to provide cutting planes along rows R1, R2, R3 . . . of posts 56 in sequence. This results in correct shaping of the transverse sides 81 of the posts 56. Thereafter, the jig 80 and posts 56 are rotated about axis B and the process repeated for the columns of the posts 56 to provide correct shaping of the longitudinal sides 82 of the posts 56. Usually several cuts per each post 56 are needed. Since the sides of each post 56 are smaller at the top than the bottom, indexing of the cutter 79 over an arc at one end of a row or column of the posts 56 is needed for each row or column cut.

FIG. 20 indicates how circular posts 56' can be constructed. In lieu of indexing the cutter 79 as previously mentioned, viz., to form four cuts (two longitudinal and two transverse cuts per post 56 of FIG. 19), the cutter 79' of FIG. 20 can be indexed about a central axis C1, C2, C3 . . . of the posts 56'. As a result, the cross section of the post 56' would be circular but the radius thereof would progressively decrease toward the apex 84 of each post 56'. After the master bracket 10, 10' has been machined, such master is used to form the mold in conventional manner, the inverse mold then being ready for production.

Note that in the shaping of the cavities of the mold, the resulting side walls of the mold cavities (whether to provide the rectangular or square cross section posts 56 of FIG. 19 or the circular cross section posts 56' of FIG. 20) are larger at the bottom than at the top. Such shaping speeds release of the brackets 10, 10' from the mold since the posts 56, 56' of each of the molded brackets 10, 10' are larger at the bottom than at the top section.

The brackets 10, 10' of the invention are preferably molded in a muli-cavity mold as integral units using metal injected molding (MIM) techniques. Provision of such brackets, viz., as integral units, allows each to be a miniature, strong and accurately reproduced unit at reasonable cost.

In the sintering process, various conventional processes can be used after the wax and/or thermoplastic binders and lubricants have been removed from the parts. In one process I know of, the wax is removed by a solvent and the remaining plastic binder is thermally removed during a controlled heat up of the furnace during sintering (a combination deplasticizing and sintering step) over a relatively long time period, say 3-5 days. In another process, the wax is removed in air at about 350 degrees F. over a 1 to 2 day period. Such removal step oxidizes the part imparting extra strength. Sintering at conventional temperatures in a closed vessel in a controlled atmosphere of argon and hydrogen follows. In yet another process, methylcellulose along with small amounts of water, glycerine and boric acid, are used as the binder. After the parts are molded, the water is removed by dry heat at 250 degrees F. Sintering using belt, pusher or vacuum furnaces, follows in which the methylcellulose is easily removed during furnace heat up since the latter breaks down at such temperature and follows the channels in the part created by the evaporated water. In still another process, the binders and lubricants are removed in a single stage vacuum furnace. The parts are sintered at temperatures of 1100 to 1300 degrees C.

The metal powder is stainless steel alloy having a particle size of less than 6 microns.

In working the posts 56, 56' after the molding and sintering has been completed, a coining operation 90 is used as shown in FIGS. 17, 18. Such operation 90 is at ambient temperature and results in the re-formation of the pre-formed parameter edges 61 of the posts 56. The goal of the coining operation 90: formation of hooded, mushroom-shaped buttons 63 of FIGS. 4 and 5 from upright edges 61 in a single stamping operation.

Referring to FIG. 17, the male member 100 of jig 101 is seen to be attached to stamping arm 102 of a stamping machine. The arm 102 is mechanically driven in the direction of arrow 91 so as to move a short distance say 0.003 inches downward relative to female member 104. Such movement places waffle-like working surface 105 of the male member 100 of FIG. 18 into contact with sharp parameter edges 61 of the posts 56. Since working surface 105 of the male member 100 is correctly shaped to provide the desired finished buttons 63, the amount of movement determines the shape of the buttons 63.

Movement of the male member 100 is controlled so the apex 106 of the crest section 107 of the working surface 105—at the end of the movement of the stamping arm 102—is above the original height of the post 56 but the arcuate shape of the edges of the crest 107 are below such original height. The result is the deformation of the sharp parameter edges 61 into a series of hooded, mushroom-shaped buttons 63 shown in phantom line, in which the sintered metal comprising each original sharp edges 63 of each post 56 is forced to conform to the shape of the crest section 107 of the male jig member 100. The jig 101 is manufactured to usual engineering standards. The female member 104 is provided with a series of cavities (not shown) to retain the bracket(s) 10 in correct alignment with the male member 100 during rectilinear movement of the latter. A series of male studs (also not shown) in alignment with female openings in the members also aid to keep the male member 100 aligned with the female member 104.

After the molded bracket 10 has been worked in the coining operation 90, the worked bracket 10 of the invention is next placed in a tumbler having an abrasive material to remove sharp edges and smooth the surfaces of the bracket 10. Smoothing of the sintered surfaces of the brackets 10 is desirable for aesthetic reasons and for the comfort of the wearer. Thereafter the brackets 10 can be placed in a second abrasive medium for polishing. During polishing, the surfaces of the bracket 10 are further smoothed to the desired degree of luster. Both smoothing operations are inexpensive and very effective from an aesthetic point of view.

SECOND EMBODIMENT

Figure 11:
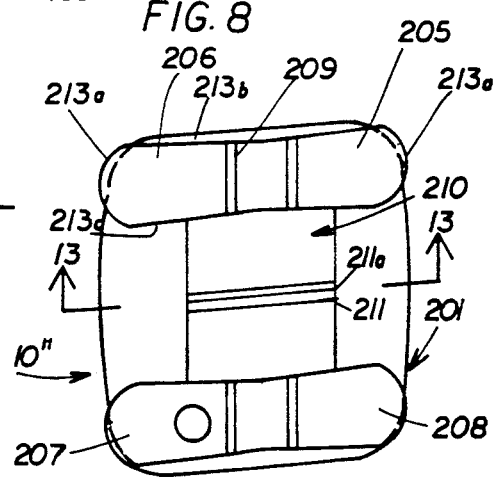
FIG. 11 is a detail top elevation view of another embodiment of the bracket of the invention in which the archwire assembly, adhesive and patient's tooth have been omitted.
Figure 13:
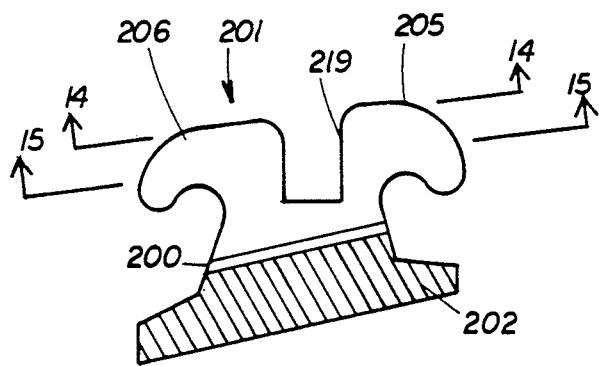
FIG. 13 is a section taken along line 13—13 of FIG. 11.
Figure 12:
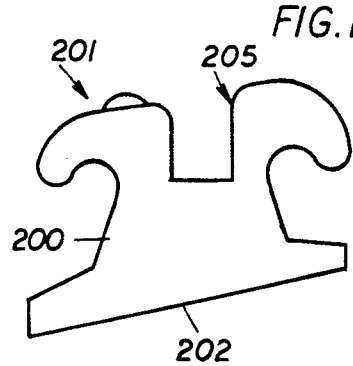
FIG. 12 is a side elevation of the embodiment of FIG. 11.

FIGS. 11–16 shows a high gingival wing profile bracket 10″ incorporating raised posts as previously described. In FIGS. 11 and 12, the bracket 10″ includes a gingivally positioned side surface 200 that provides greater space for the orthodontist to more easily apply the bracket 10″ to the tooth of the wearer.

The bracket 10″ also includes an labiobuccally extending, archwire portion 201 that is opposite to the buccolingually positioned tooth abutting surface 202, such archwire portion 201 including a plurality of L-shaped wing members 205, 206, 207 and 208. The wing members 205–208 are spaced along row and column directions to provide slot 209 and intersecting groove 210 therebetween. The slot 209 is mesodistally extending in its attachment position to capture a straighwire (not shown) as well as defines a reference line (relative to the occlusal plane) by which the bracket 10′ can be correctly positioned in that dimension. The groove 210 provides a sight line via apex 211a of a VEE 211 (see FIG. 11) for proper positioning of the bracket 10′ in a second dimension. The shape of such wing members 205–208 is not rhomboidal.

Note in FIGS. 11, 14 and 15 that any section through the occlusally, gingivally and lingually positioned surfaces 213a, 213b and 213c of the pair of wing members 205, 206 or 207, 208 (as measured from a base reference plane) divides the occlusally positioned surfaces 213a into pairs of arcuate and planar edges. However, the apexes of the arcuate edges still provide positional guides since a line through the apexes are still parallel to the sight line previously mentioned. Yet sharp parameter edges conventionally a part of rhomboidal shaped wing members are avoided.

FIG. 16 shows the shape and character of the tooth abutting surface 202. Note that extending from curved base 220 of the tooth abutting surface 202 are a series of lingually extending, raised posts 221 that have characteristics and are shaped as previously described. Sufficient to say, that the posts 221 are integrally formed with respect to the curved elongated planar base 220 and define roof sections 221a that originally include sharp parameter edges 222 that were smaller in all directions than the root sections of the posts 221. Such edges 222 although originally smaller in all directions are re-shaped as set forth above to form inverted, anchor-like, hatted buttons or cusps that are larger in all directions than the root sections of the posts 221. As a result, the total bondable surface area formed by the worked posts 221 and the segmented curved base 220, form a modified scalloped tooth abutting surface generally indicated at 225. Such scalloped abutting surface 225 is in three dimensions radiating from any of the posts 221 in row, columnar and lateral directions for improved disconnectable attachment of the bracket 10″ in the manner previously described.

Modifications and variations of the invention may be made to the embodiments set forth herein without departing from what is regarded as the invention as defined in the following claims.

What is claimed is:

1. A miniature orthodontic appliance that is smaller than conventional appliances comprising a bracket formed as a mono-block unitary structure and including an archwire portion adapted to receive a straight-wire, an elongated base pad portion integrally attached to said archwire portion and having a tooth abutting surface positioned opposite to said archwire portion, said tooth abutting surface having a curved base surface and a plurality of raised posts extending from said curved base surface, each raised post including a root section integrally formed with said curved base surface and an enlarged inverted button section at an end remote from said root section, each of said button sections including a parameter edge that was originally smaller in all directions than said root section but which has been worked into an enlarged edge that is larger in all directions than said root section whereby a modified scalloped tooth abutting surface is formed across said button sections for improved disconnectable attachment of said appliance to a patient's tooth, said scalloped tooth surface across said button sections of said raised posts comprising a series of repeating anchor segments extending in row, column and lateral directions between adjacent posts, each of said anchor segments including end sections between said adjacent posts and an enlarged Tee-shaped section, also formed therebetween, each of said button sections comprising an apex region remote from said curved base surface of said tooth abutting surface, sloped roof sections attached to and sweeping from said apex region at an angle, and eave segments attached to said sloped roof sections overhanging said curved base surface between adjacent posts.

2. The orthodontic appliance of claim 1 in which each of said button sections is formed of and is associated with said parameter edge.

3. The orthodontic appliance of claim 2 in which said Tee-shaped section includes first and second arms formed between (a) said curved base surface of said tooth abutting surface positioned between said adjacent posts, (b) upright surfaces of said adjacent posts at right angles to said curved base surface and (c) surfaces associated with said eave segments overhanging said curved base surface.

4. The orthodontic appliance of claim 3 in which said Tee-shaped section includes a third arm formed and defined by said roof sections of adjacent button sections between said eave segment and said apex regions of adjacent button sections.

5. The orthodontic appliance of claim 4 in which said end sections of each of said anchor segments of said modified scalloped tooth abutting surface is defined by and is positioned adjacent to said apex regions of adjacent posts.

6. A process for providing an orthodontic appliance including a mono-block unitary bracket having an archwire portion adapted to receive a straightwire, an elongated base pad portion integrally attached to said archwire portion having a tooth abutting surface positioned opposite to said archwire portion, said tooth abutting surface having a plurality of raised posts extending from a curved base surface, each raised post including a base coincident with said curved base surface and an outer parameter edge initially and originally smaller in all directions than said base but after working is larger than said base in all directions, said process comprising the following steps:
- (a) molding said mono-block bracket as a unitary piece using metal injected molding (MIM);
- (b) working said raised posts of said bracket into a series of mushroom-shaped buttons, each of said buttons including a parameter edge greater in dimension in all directions than the base of its post, said parameter edge including an apex region, sloped roof sections attached to and sweeping from said apex region at an angle, and eave segments attached to said sloped roof sections overhanging said curved base surface between adjacent posts, whereby a bonding adhesive adapted to be placed between said base surface of said tooth abutting surface including said parameter edges of said buttons and a tooth of a patient, provides bonding strength sufficient for said appliance to withstand the stresses of ordinary and usual activities of the patient.

7. The process of claim 6 in which step (a) is further characterized by molding said bracket using a composition comprising sinterable steel particles and plastic binders followed by sintering said steel particles at conventional sintering temperature in which at least a portion of said plastic binders is simultaneously removed.

8. The process of claim 7 in which said sinterable steel particles are each less than 6 microns.

9. The process of claim 7 in which said sintering temperatures are in a range of 1100 to 1300 degrees C.

10. The process of claim 6 in which step (b) is further characterized by said parameter edge of each of said posts that includes said apex region, sloped roof sections and said eave segments overhanging said curved base surface between adjacent posts, being formed by coining.

11. The process of claim 10 in which said coining comprises driving an elongated male member of a jig having a waffle working surface into contact with said posts and releasing said male member from contact with said parameter edges of said posts.

12. The process of claim 11 in which said coining of said edges of said posts is further characterized by said edges being in a sintinered state and said coining being carried out at ambient temperature.

13. The process of claim 12 in which said coining includes the precursor step of fitting said mono-block bracket rigidly within a female member of said jig in working alignment with said male member.

14. in a miniature orthodontic appliance that is smaller than conventional appliances, the combination comprising a bracket formed as a mono-block unitary structure adapted to be attached to a patient's tooth and including a labiobuccally positioned archwire portion, a mesiodistally extending straight wire adapted to be received in said archwire portion, a base pad portion integrally attached to said archwire portion and having a buccolingually extending tooth abutting surface positioned opposite to said archwire portion, said tooth abutting surface having a plurality of raised posts, extending from a curved base surface opposite to said archwire portion each raised post including a base integrally formed with respect to said curved base surface of said tooth abutting surface and a remote section including a parameter edge at a remote end thereof initially and originally smaller in all directions than said base but which has been worked into a mushroom shaped button having a parameter edge greater in all directions than said base of said raised post, a non-toxic orthodontic adhesive adapted to be placed between said tooth abutting surface and a tooth of a patient, whereby a bond of sufficient strength for said combination to withstand the stress of usual activities is provided, said worked raised posts defining a scalloped tooth abutting surface wherein said adhesive is placed between said scalloped tooth abutting surface and said patient's tooth to define a series of repeating anchor segments extending in row, column and lateral directions between adjacent posts, each of said anchor segments including end sections and an enlarged Tee-shaped section formed therebetween, each of said buttons comprising an apex region remote from said curved base surface of said tooth abutting surface, a sloped roof section attached to and sweeping from said apex region at an angle, and an cave segment attached to said sloped roof section overhanging said curved base surface between adjacent posts.

15. The combination of claim 14 in which said Tee-shaped section includes first and second arms formed between (a) said curved base surface of said tooth abutting surface positioned between said adjacent posts, (b) upright surfaces of said adjacent posts at right angles to said curved base surface and (c) surfaces associated with said eave segments overhanging said curved base surface.

16. The combination of claim 15 in which said Tee-shaped section includes a third arm formed defined by said roof sections of adjacent buttons.

* * * * *